United States Patent [19]

Kao et al.

[11] 4,247,465

[45] Jan. 27, 1981

[54] PREPARATION OF ALKYLENE CARBONATES FROM OLEFINS

[75] Inventors: Jar-Lin Kao, Cherry Hill; Gregory A. Wheaton, Swedesboro, both of N.J.; Harold Shalit, Bala Cynwyd, Pa.; Ming N. Sheng, Cherry Hill, N.J.

[73] Assignee: Atlantic Richfield Company, Los Angeles, Calif.

[21] Appl. No.: 68,996

[22] Filed: Aug. 23, 1979

[51] Int. Cl.³ .................. C07D 317/36; C07D 317/38
[52] U.S. Cl. .................................................. 260/340.2
[58] Field of Search ...................................... 260/340.2

[56] References Cited

U.S. PATENT DOCUMENTS

| | | | |
|---|---|---|---|
| 3,025,305 | 3/1962 | Verdol | 260/340.2 |
| 4,009,183 | 2/1977 | Fumagalli et al. | 260/340.2 |

*Primary Examiner*—Norma S. Milestone
*Attorney, Agent, or Firm*—Delbert E. McCaslin

[57] ABSTRACT

A process for the preparation of a cyclic alkylene carbonate ester which comprises reacting in a liquid phase a cyclic or linear olefin having from 2 to 15 carbon atoms with carbon dioxide at a temperature of from 30° to 160° C., at a total pressure of from 100 to about 2,000 psig and a pH value of between about 4 and 8, in the presence of oxygen or an oxygen-containing gas and a catalytic amount of a mixture of (a) iodine or an iodide of a metal selected from Groups IA, IB, IIA, IIB, VB, VIIB and VIII of the Periodic Table of Elements, (b) a carbonate of a metal selected from Groups IB, IIA, IIB and VIII of the Periodic Table of Elements, (c) a catalytic iron compound and (d) a catalytic soluble cupric salt, and recovering resulting cyclic alkylene carbonate ester.

5 Claims, No Drawings

PREPARATION OF ALKYLENE CARBONATES FROM OLEFINS

BACKGROUND OF THE INVENTION

The cyclic carbonate esters of vicinal diols are well known in the art and may be prepared by reacting the corresponding chlorohydrins with either sodium bicarbonate under carbon dioxide pressure or with an alkali metal carbonate. Such esters can also be produced by the reaction between vicinal chlorohydrins and diethylamine under carbon dioxide pressure. All of these processes require the use of a stoichiometric amount of base.

Another route for the preparation of cyclic alkylene carbonate esters involves the reaction between an alkylene epoxide and carbon dioxide at high pressure in liquid phase in the presence of a catalyst. Typical catalysts include quaternary ammonium halides, quaternary ammonium hydroxides, sodium bicarbonate, ion exchange resins, bis-(aminoethoxy)tin compounds and polyhalogenated 5- or 6-membered ring hydrocarbons. Such processes as these require the use of expensive alkylene epoxide as the starting material for the cyclic carbonate ester production.

Two routes for production of cyclic carbonate esters directly from olefins have appeared in the literature. According to U.S. Pat. No. 3,025,305, an olefin, carbon dioxide and oxygen are reacted in the liquid phase in the presence of a dual catalyst system. One component of the catalyst is a salt or other compound of a heavy metal and the second catalyst component is a quaternary ammonium hydroxide or halide. According to U.S. Pat. No. 4,009,183, cyclic carbonate esters are produced by the reaction between an olefin, carbon dioxide and oxygen in the presence of iodine or a metal iodide and an oxygen carrier such as activated manganese dioxide or sodium nitrite. In each of these routes the rate of carbonate ester formation is slow. In the second route, a second step is required in order to regenerate the oxygen carrier which is used in stoichiometric excess.

SUMMARY OF THE INVENTION

The present invention relates to the preparation of cyclic alkylene carbonate esters and comprises reacting in a liquid phase a cyclic or linear olefin having from 2 to 15 carbon atoms with carbon dioxide at a temperature of from 30° to 160° C., at a total pressure of from 100 to about 2,000 psig and a pH value of between about 4 and 8, preferably between about 6 and 7, in the presence of oxygen or an oxygen-containing gas and a catalytic amount of a mixture of (a) iodine or an iodide of a metal selected from Groups IA, IB, IIA, IIB, VB, VIIB and VIII of the Periodic Table of Elements, (b) a carbonate of a metal selected from Groups IB, IIA, IIB and VIII of the Periodic Table of Elements, (c) a catalytic iron compound, and (d) a catalytic soluble cupric salt, and recovering resulting cyclic alkylene carbonate ester.

The process of the present invention produces the cyclic alkylene carbonate esters with high selectivity at high rates directly from the corresponding olefin in one step without the operational problems associated with the prior art processes.

DETAILED DESCRIPTION OF THE INVENTION

In accordance with the present invention, a cyclic or linear olefin having from 2 to 15 carbon atoms is reacted in an autoclave or any other pressure reactor with carbon dioxide and oxygen at elevated temperature and pressure in the presence of a catalyst comprising (a) iodine or an iodide of a metal selected from Groups IA, IB, IIA, IIB, VB, VIIB and VIII of the Periodic Table of Elements, (b) a carbonate of a metal selected from Groups IB, IIA, IIB and VIII of the Periodic Table of Elements, (c) a catalytic iron compound and (d) a catalytic soluble cupric salt. The order of addition of the reactants, catalysts, solvents, etc. is not critical and the process may be carried out batchwise or continuously.

Any cyclic or linear olefin having from 2 to 15 carbon atoms may be employed in the present process. Preferably, the olefin contains from 2 to about 6 carbon atoms and even more preferably, the olefin is an $\alpha$-olefin, i.e., contains a terminal carbon-to-carbon double bond. Ethylene, propylene, butylenes, pentenes, hexenes and cyclohexene are examples of especially preferred olefins.

The metal iodides which may be employed in the catalytic system for this process are selected from Groups IA, IB, IIA, IIB, VB, VIIB, and VIII of the Periodic Table of Elements. The metal iodides which may be employed include, for example, lithium iodide, sodium iodide, potassium iodide, cuprous iodide, calcium iodide, magnesium iodide, zinc iodide, cadmium iodide, vanadium iodide, manganese iodide, iron iodide, cobalt iodide, and the like. The amount of metal iodide which may be employed in this invention is generally in the range of from 0.5 to 90 mole percent of the olefin reactant. Preferably the amount of metal iodide to be employed is between 15 to 50 mole percent of the olefin employed.

The metal carbonates employed in the catalyst component mixture are in amounts of about 5 to 50 mole percent, preferably from about 10 to 30 mole percent of the olefin employed. Suitable metal carbonates for use in the process of this invention include, for example, cupric carbonate dihydroxide, calcium carbonate, magnesium carbonate, barium carbonate, zinc carbonate and the like. The use of a metal carbonate as an integral part of the catalytic system is for the purpose of adjusting the pH values in the range of 4 to 8, preferably 6 to 7, in order to obtain a high selectivity to alkylene carbonate. Under the reaction conditions, the metal carbonate is regenerated in situ from the reaction of the corresponding metal ion with carbon dioxide.

In order to achieve a high productivity rate, an iron compound is needed. The iron compounds are employed in the catalyst component mixture in amounts of about 1 to 35 mole percent, preferably from 5 to 25 mole percent of the olefin employed. Suitable iron compounds for use in the process of this invention include, for example, ferrous iodide, ferrous and ferric chlorides, ferrous and ferric bromides, ferrous and ferric nitrates, ferrous and ferric sulfates, ferrous and ferric oxides, hydrous ferric oxide, and the like.

As shown by the examples, the addition of a soluble cupric salt to the catalytic system containing iron catalyst increases the reaction rate. The soluble cupric salt is employed in the catalyst component mixture in amounts of about 0.5 to 25 mole percent, preferably from about 2 to 10 mole percent of the olefin employed, and suitable cupric salts for use in the process of this invention include, for example, cupric bromide, cupric chloride, cupric perchlorate, cupric nitrate, cupric sulfate, and the like.

Solvents suitable for use in the process of this invention to form the reaction medium are, for example, water or mixtures of water and a water-miscible organic solvent. Organic solvents which are suitable for use in this process include, for example, acetonitrile, N,N-dimethylformamide, dioxane, propylene-1,2-diol, sulfolane, tertiary butyl alcohol, tetrahydrofuran, and the like. The ratio of the volume of water to the volume of organic solvent which may be employed is not critical but preferably is from about 10:1 to about 1:10. More preferably, it ranges between about 5:1 to about 1:5.

The reaction temperature at which the process may be operated may vary between about 30° C. and 160° C. The preferred temperature is between about 70° C. and 140° C.

The partial pressure of carbon dioxide to be employed in the process of this invention will generally vary between about 15 and 1000 psia. The preferred carbon dioxide partial pressure is between about 100 to about 700 psia. Liquid carbon dioxide at 800 psia is also a preferred feature of the present invention.

The amount of oxygen to be employed in the process of this invention must, of course, be at least the stoichiometric amount required with respect to the starting olefin, but a stoichiometric excess of oxygen may be employed. A slight stoichiometric excess of oxygen is preferably employed in the process of this invention. The oxygen may be employed as pure oxygen, may be in the form of an oxygen-containing gas such as air, or may be diluted with an inert gas such as nitrogen, argon, etc. The partial pressure of oxygen which may be employed in the process of this invention preferably varies between about atmospheric and about 400 psia and is more preferably between about 50 and 200 psia. The partial pressure of oxygen should be regulated so as to avoid the formation of explosive mixtures during the course of the carboxylation reaction.

The total pressure to be used in the process of this invention may vary between about 100 to about 2000 psig. The preferred total pressure to be used in the process of this invention is between about 800 and 1600 psig.

The following examples illustrate but do not limit the scope of the present invention.

EXAMPLE 1

Into a 500 ml Hastelloy stirred autoclave, there was introduced 8.61 g of ferrous iodide, 3.32 g. of cupric sulfate, 9.24 g of potassium iodide, 11.14 g of calcium carbonate, 30 ml of sulfolane, 120 ml of water, 16.0 g of propylene, 600 psia of carbon dioxide, and 65 psia of oxygen. The reaction mixture was heated at 120° C. for 5 hours. Oxygen (10 psia) was added after each hour of reaction. After cooling the reaction mixture to 25° C., the pressure was slowly released. Solid catalyst was recovered by filtration. The liquid product was analyzed by gas chromatography. The presence of 73 mmoles of propylene carbonate, 59 mmoles of propylene glycol, 13 mmoles of propylene iodohydrins, 12 mmoles of acetone, and 3.0 mmoles was measured. The productivity rate amounted to 0.213 mole/liter-hour.

EXAMPLES 2-5

Four runs were carried out employing the same reaction conditions and catalyst compositions as Example 1 except that the organic co-solvent was varied. The experimental results are shown in Table I.

As can be seen from the results of Examples 1-5, the us of organic co-solvent increases the productivity rate relative to using water alone.

TABLE I

| Run No. | 2 | 3 | 4 | 5 |
|---|---|---|---|---|
| H$_2$O (ml) | 150 | 120 | 120 | 120 |
| Organic co-solvent (ml) | — | N,N-dimethyl-formamide | Di-oxane | pyrrolidone |
|  | None | 30 | 30 | 30 |
| Products (mmoles) |  |  |  |  |
| Propylene carbonate | 42 | 66 | 60 | 66 |
| Propylene glycol | 37 | 41 | 45 | 45 |
| Propylene iodohydrins | 8 | 17 | 15 | 15 |
| Acetone | 16 | 8 | 8 | 10 |
| Propanal | 2 | 1 | 1 | 3 |
| Productivity Rate (mole/liter-hour) | 0.139 | 0.178 | 0.173 | 0.187 |

EXAMPLE 6

This example showed that the productivity rate was increased by cutting the amount of solvent used in Example 1 in half. After 3.5 hours under the same reaction conditions as Example 1, the oxidative carboxylation reaction produced 47 mmoles of propylene carbonate, 24 mmoles of propylene glycol, 13 mmoles of propylene iodohydrins, 12 mmoles of acetone, and 2 mmoles of propanal. The productivity rate was 0.374 moles/liter-hour.

EXAMPLE 7

Increasing the amount of potassium iodide used in Example 3 from 9.24 g to 37.0 g improved the yield of propylene carbonate. After 3 hours, the reaction gave 70 mmoles of propylene carbonate, 4 mmoles of propylene glycol, 15 mmoles of propylene iodohydrins, 4 mmoles of acetone, and 1 mmole of propanal. The productivity rate was 0.212 mole/liter-hour.

EXAMPLE 8

A run was carried out under the reaction conditions of Example 1 in the absence of cupric sulfate and sulfolane. The reaction yielded 48 mmoles of propylene carbonate, 6 mmoles of propylene glycol, 15 mmoles of propylene iodohydrins, 5 mmoles of acetone, and 2 mmoles of propanal. The productivity was 0.101 mole/liter-hour. In a comparison of Example 2 with Example 8, the addition of cupric sulfate to the catalyst system increases the reaction rate.

EXAMPLES 9-10

A series of runs were carried out using the catalysts listed below to determine the yield of propylene carbonate from the carboxylation of propylene. Reaction conditions were essentially the same as used in Example 1. The experimental results are shown in Table II.

TABLE II

| Run No. | 9 | 10 |
|---|---|---|
| Charge (mmoles) |  |  |
| Propylene | 381 | 381 |
| FeI$_2$ | 27.8 | 27.8 |
| Cu(NO$_3$)$_2$ · 3H$_2$O | 13.3 | None |
| CuSO$_4$ · 5H$_2$O | None | 13.3 |
| LiI | 55.7 | None |
| CaI$_2$ | None | 27.8 |
| CaCO$_3$ | None | 111.3 |

TABLE II-continued

| Run No. | 9 | 10 |
| --- | --- | --- |
| $CuCO_3 \cdot Cu(OH)_2$ | 55.7 | None |
| $H_2O$/Sulfolane (ml) | 120/none | 60/15 |
| Products (mmoles) | | |
| Propylene carbonate | 41 | 94 |
| Propylene glycol | 34 | 28 |
| Propylene iodohydrins | 8 | 15 |
| Acetone | 15 | 22 |
| Propanal | 3 | 4 |
| Productivity Rate (mole/l-hr) | 0.135 | 0.436 |

EXAMPLE 11

The experimental procedure of Example 8 was repeated except that 200 psia of oxygen was charged initially. The oxidative carboxylation reaction produced 72 mmoles of propylene carbonate, 11 mmole of propylene glycol, 16 mmoles of propylene iodohydrins, 7 mmoles of acetone, and 2 mmoles of propanal. The productivity rate amounted to 0.144 mole/liter-hour.

EXAMPLE 12

The experimental procedure of Example 11 was employed except that calcium carbonate was omitted, and the reaction temperature was 100° C. The oxidative carboxylation reaction gave 12 mmoles of propylene carbonate, 46 mmoles of propylene iodohydrins, 5 mmoles of acetone, 3 mmoles of propanal. The productivity rate was 0.089 mole/liter-hour.

EXAMPLE 13

Into a 500 ml Hastelloy stirred autoclave, there was introduced 10.6 g of cuprous iodide, 9.24 g of potassium iodide, 6.15 g of cupric carbonate dihydroxide, 150 ml of water, 16.0 g of propylene, 600 psia of carbon dioxide, and 200 psia of oxygen. The reaction mixture was heated at 120° C. for 5 hours. The workup procedure was essentially the same as described in Example 1. The reaction produced 41 mmoles of propylene carbonate, 7 mmoles of propylene glycol, 7 mmoles of propylene iodohydrins, 7 mmoles of acetone, 2 mmoles of propanal, and 1 mmole of propylene oxide. The productivity rate amounted to 0.086 mole/liter-hour. In a comparison of Example 11 with Example 13, the use of ferrous iodide gave a higher productivity rate than that obtained using cuprous iodide.

We claim:

1. A process for the preparation of a cyclic alkylene carbonate ester which comprises reacting in a liquid phase a cyclic or linear olefin having from 2 to 15 carbon atoms with carbon dioxide at a temperature of from 30° to 160° C., at a total pressure of from 100 to about 2,000 psig and a pH value of between about 5 and 7 in the presence of oxygen or an oxygen-containing gas and a catalytic amount of a mixture of
    (a) from about 0.5 to 90 mole percent of said olefin reactant of an alkali metal or an alkaline earth metal iodide,
    (b) from about 5 to 50 mole percent of said olefin reactant of a cupric carbonate dihydroxide or calcium carbonate,
    (c) an iron compound selected from the group consisting of ferrous iodide, ferrous and ferric chlorides, ferrous and ferric bromides, ferrous and ferric nitrates, ferrous and ferric sulfates, ferrous and ferric oxides and hydrous ferric oxide in an amount of from about 1 to 35 mole percent of said olefin reactant and
    (d) from about 0.5 to 25 mole percent of the olefin reactant of a soluble cupric salt and recovering the desired cyclic alkylene carbonate ester.

2. The process of claim 1 wherein said olefin is propylene.

3. The process of claim 1 wherein said total pressure is from about 800 to 1,600 psig.

4. The process of claim 1 wherein (d) is selected from the group consisting of cupric bromide, cupric chloride, cupric perchlorate, cupric nitrate and cupric sulfate.

5. A process according to claim 1 wherein the temperature is between about 70° and 140° C.

* * * * *